(12) United States Patent
Zeng et al.

(10) Patent No.: US 7,195,772 B2
(45) Date of Patent: Mar. 27, 2007

(54) AMINO-ACID IODINE COMPLEX

(76) Inventors: Xiongfei Zeng, Sandong, Huizhoucity, Guangdong 516025 (CN); Jiang Zeng, Sandong, Huizhoucity, Guangdong 516025 (CN); Yan Zeng, Sandong, Huizhoucity, Guangdong 516025 (CN)

( * ) Notice: Subject to any disclaimer, the term of this patent is extended or adjusted under 35 U.S.C. 154(b) by 768 days.

(21) Appl. No.: 10/312,521

(22) PCT Filed: Oct. 19, 2001

(86) PCT No.: PCT/CN01/01490

§ 371 (c)(1),
(2), (4) Date: Feb. 10, 2003

(87) PCT Pub. No.: WO02/088068

PCT Pub. Date: Nov. 7, 2002

(65) Prior Publication Data

US 2003/0171598 A1    Sep. 11, 2003

(30) Foreign Application Priority Data

Apr. 28, 2001   (CN) ................................. 01 1 14666

(51) Int. Cl.
*A01N 25/00*   (2006.01)
*C07C 323/00*  (2006.01)
(52) U.S. Cl. ........................ 424/405; 562/556; 562/559
(58) Field of Classification Search ...................... None
See application file for complete search history.

(56) References Cited

U.S. PATENT DOCUMENTS 2,517,651 A * 8/1950 Frost ........................... 424/601

FOREIGN PATENT DOCUMENTS

JP   10203916   *  8/1998

OTHER PUBLICATIONS

Merck, The Merck Index, 10th Edition, 1983, Merck & Co., Inc., Rahway, N.J. pp. 726-727.*
Baraud, Chimie Analytique, Direct and Indirect Iodometry in the Study of Proteins, 1966, 48(4) pp. 179-187, CAS abstract.*
Chang, American Journal of Physiology, Effect of Iodinated Casein on Production of Vitamin B-12 and Folic Acid Deficiency in Rats, 1969, 216(1), pp. 11-15, CAS abstract.*
Singh, V. et al. "Interaction of Some Biomolecules with π and σ-Acceptors". Monatshefte Fur Chemie 117, pp. 345-350 (1986).
Abu-Eittah, R.H., et al. "Charge Transfer Complexes of Some Amino Acids With Iodine . . . ". Zeitschrift für Physikalische Chemie, Bd. 178, (1992) pp. 67-86.

* cited by examiner

*Primary Examiner*—Paul A. Zucker
(74) *Attorney, Agent, or Firm*—Ladas and Parry LLP

(57) ABSTRACT

An amino-acid iodine complex, viz. amino-acid amino-carboxyl iodine complex, was provided wherein its coordinate center is iodine molecule, complex reagent is amino-acid, sites of complexing reaction are amino and carboxyl groups of amino-acid. The complex can be used for the production of feedstuff, food additive, disinfectant, antiseptic and medicament. Also provided is a method for the production of said complex comprising opening the inner-complex ring of amino-acid by acid catalysis and allowing the amino-acid to combine with iodine molecule to form an amino-acid amino-carboxyl iodine complex; because amino-acid is a nutriment and amino-carboxyl complex is achieved, their introduction not only increases the nutritional function of the complex and improves the stability of iodine, but also is beneficial to the environment protection and enhances the disinfecting activity against viruses and bacteria.

19 Claims, No Drawings

AMINO-ACID IODINE COMPLEX

FIELD OF THE INVENTION

The present invention relates to the field of chemistry, especially, amino-acid iodine complexes used for preparing feedstuff, food additive, disinfectant, germicide and medicament, as well as methods for the preparation thereof.

BACKGROUND OF THE INVENTION

Iodine is one of the essential nutrients, iodine tincture has been used as disinfectant for a long history. Iodine has also been used as a particularly-effective medicament for the treatment of goiter. However, the main disadvantage of iodine is that it can be sublimated easily, and thus is unstable. To prepare stable iodine, Germany Patent DE-2941387 and DE-3060935 provide polyvinyl pyrrolidone-iodine (PVP-I), which is a kind of complex wherein PVP is complex reagent. The stability of PVP-I is better than iodine, but said complex reagent PVP is not required to animals. The iodine complex prepared by quaternary ammonium salt has the same defect.

Vinod Singh and Ram Sahai(Monatshe fur Chemie 117, 345–350, 1986) had investigated the charge transfer between several amino-acids, e.g phenylalanine, alanine, tryptophan and iodine, they considered that the charge transfer complex has been formed as the result. Rafie H. et al. (Zeitschrift fur Physikalische Chemie, BD. 178, 67–86, 1992) had investigated the process of forming the charge transfer complex between histidine, tryptophan and iodine dissolved in the solution potassium iodide, found that the pH value remains unchanged during the process, and the process only involves the amino group of the amino-acid, but not the carboxyl group. Electrode material disclosed in JP 63143750 is also a kind of charge transfer complex formed between amino-acid and iodine. The common characteristic of the above mentioned materials is that the complex, which is a kind of ionic triiodide-complex of amino-acid, was formed by reaction of ionic triiodide-complex ($I^-_3$) as reactant in which iodine as electronic acceptor, with the amino group of amino-acid as electronic donor. If the amino-acid is in excess, fading would occur and the iodine will lose the activity of disinfection. The introduction of iodic ion ($I^-$) in large amount produces no favorable effect on the activity of disinfection, but increases the cost of manufacture.

The objective of the present invention, aimed at the defects of prior art, is to provide an iodine complex wherein the iodine is stable, the complex reagent can also be a nutrient, and iodine molecule can directly react with amino-acid without adding an iodic ion. It is also the objective of the present invention to provide a process for the production of said complex.

It is now discovered that the amino-acid and iodine are the dialectic system, amino-acid being not only the electronic donor, but also the electronic acceptor; iodine being the electronic acceptor, and electronic donor as well. Iodine is a non-metal, but it possesses some characteristics of a metal. An amino-acid is a complex reagent, and a nutrient too. Amino-acids are natural material, so when they are used as complex reagent, they can increase the ability of disinfection through the metabolism of organism. Both the amino group and the carboxyl group of an amino-acid can combine with iodine molecule simultaneously under suitable conditions such as temperature, solvent and catalyst etc. to form a stable amino-acid iodine complex, viz. amino-acid amino-carboxyl iodine complex.

DESCRIPTION OF THE INVENTION

The amino-acid iodine complexes according to the present invention have the general formula (I):

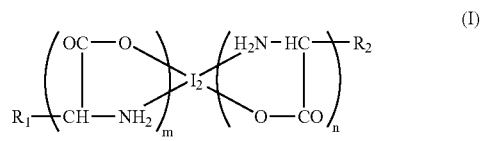

wherein the coordinate center is the iodine molecule, the complex reagent is an amino-acid, and wherein $R_1$ and $R_2$ are side-chain groups of the amino-acid, m and n are the numbers of the amino-acid, respectively.

$R_1$ and $R_2$ can be the same or different groups, the complex reagent is composed of the same amino-acids when $R_1$ is equal to $R_2$, and the complex reagent is composed of different amino-acids when $R_1$ is different from $R_2$. When $R_1$ and $R_2$ are H, the amino-acid in formula (I) is glycine, when $R_1$ and $R_2$ are $CH_3$, the amino-acid in formula (I) is alanine, and so on.

As the complex reagent, the amino-acid can be the same and/or different simple amino-acid, such as alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr) and valine (Val).

Besides the above mentioned simple amino-acids, the complex reagent can also be derivative of said amino-acids, e.g. acetyl methionine, methionine hydroxyl analogs; or simple peptide formed by simple amino-acids, e.g. lysine-aspartate, lysine-glutamate; or multiplex amino-acids obtained by hydrolyzing an animal or plant protein.

Said iodine can be the oridinary iodine molecule, or its radioactive isotope.

Depends on the specific amino-acids used in the complex and its application, gram-molecular ratio of amino-acid to iodine varies generally in the range from 2 to 20, and preferably from 2 to 5.

The iodine is insoluble in water. To prepare the charge transfer complex, iodine needs to be added into the solution of iodic ion to form soluble ionic triiodide-complex ($I^-_3$), then, said ionic triiodide-complex ($I^-_3$) combines with amino group of amino-acid, but the carboxyl group does not involve in the reaction. During the process pH remains unchanged, amino-complex iodine being produced only, and the gram-molecular ratio of amino-acid to iodine being 1:1. The amino-acid is amphoteric substance, in which amino group and carboxyl group form the inner-complex salt. Hence, to prepare the complex of the present invention, the ring of inner-complex salt must be opened at first in order to expose the amino group and carboxyl group at binding sites. Subsequently, the iodine molecule ($I_2$) takes place complexing reaction with amino and carboxyl groups of amino-acid at the catalysis of an acid to form the amino-acid iodine complex, during the complexing process the proton was released, leading to pH decreasing. Generally, gram-molecular ratio of amino-acid to iodine is 2:1. Inner-complex ring can be opened by acidic substance. The acid to open the ring can be inorganic acids, for example, phosphoric acid, hydrochloric acid, and sulfuric acid; or organic acids, for example, citric acid, acetic acid, fumaric acid, and lactic acid.

In the amino-carboxyl complexing reaction of the present invention, the acid has the double functions, one of which is to open the ring, the another is to catalyze the complexing reaction.

The medium of the complexing reaction can be water, or organic solvents, such as ethanol, glycol, acetone, petroleum ether, benzyl alcohol and ethyl acetate.

According to the present invention, the reaction for the production of amino-acid iodine is carried out at a pH level of from about 1 to 5, at a temperature of from about 25 to 85° C. and for a period of from about 30 to 300 mins, preferably, the pH being maintained at a level of from about 2 to 3, the temperature being from about 40 to 50° C. and for a period of from about 150 to 200 mins. The optimal reaction condition can be pH being 4.5, temperature being 45° C., time being 200 mins.

Using the same method, the amino-acid bromine complex can also be prepared.

Compared with prior art, the present invention has following advantages:

1. Because the amino-acid is a nutrient, its introduction into the complex of course increases the nutritional function of the complex, which is also beneficial to environment.

2. The amino-acid iodine complex according to the present invention has better stability because of its being an amino-carboxyl complex with the iodine molecule as the coordinate center.

3. There are synergetic effects between iodine and amino-acid, so the disinfectant ability of iodine against bacteria and virus has increased several times.

4. The safety of amino-carboxyl iodine complex is better than PVP-I.

5. According to the present invention the amino-acid iodine is not produced by the use of ionic triiodide-complex ($I^{31}_3$), but by iodine molecule, so that its cost and toxicity are reduced significantly.

6. The applications of iodine are expended to fields such as livestock raising, farm production, medical treatment and hygiene, and nutritional medicament; It also be a potent killer for bacteria and virus, thus beneficial to the health of human and the environment.

The following examples are used to illustrate the present invention in detail, but they do not constitute limitations of the present invention in any way.

EXAMPLE 1

Preparation of Glycine Iodine

In a 250 ml round-bottom flask equipped with heating and magnetic stirring devices, 100 ml of water was added, raised the temperature up to 55° C. with stirring, then added 14 g of L-glycine. When dissolved completely, 8 g of concentrated hydrochloric acid was added, and 25 g of iodine was then introduced gradually, and the mixture was stirred for about 150 minutes, then filtrated, the filtrate was concentrated and dried to afford 36.80 g title compound.

By analyzing, the obtained product was found to have the following data:
Available iodine content: 22.1 g
L-glycine: 13.5 g.

EXAMPLE 2

Preparation of Lysine Iodine

Following a method similar to example 1, 85 ml of water was added, raised the temperature up to 75° C. with stirring, then added 24 g of lysine hydrochloride, when dissolved completely, 19 g of iodine was gradually added to the solution, and the mixture was stirred for about 130 minutes, then filtrated, the filtrate was concentrated and dried to afford 40.20 g title compound.

By analyzing, the obtained product was found to have the following data:
Available iodine content: 16.1 g
Lysine hydrochloride :23.5 g.

EXAMPLE 3

Preparation of Arginine Iodine

Following a method similar to example 1, 150 ml of water was added, raised the temperature up to 80° C. with stirring, then added 10 g of L-arginine, when dissolved completely, 1.5 g of phosphoric acid was added, and 4.4 g of iodine was then introduced gradually, and the mixture was stirred for about 110 minutes, cooled and stood for about 180 minutes, then filtrated, the filtrate was concentrated and dried to afford 13.70 g title compound.

By analyzing, the obtained product was found to have the following data:
Available iodine content: 4.0 g
Arginine :9.6 g.

EXAMPLE 4

Preparation of Asparagine Iodine

Following a method similar to example 1, 105 ml of petroleum ether was added, raised the temperature up to 30° C. with stirring, added 1.5 g of asparagine and 0.15 g of sulfuric acid, and 1.0 g of iodine was then introduced gradually, and the mixture was stirred for about 110 minutes, then filtrated, the filtrate was evaporated to remove the solvent and dried to afford 1.96 g title compound.

By analyzing, the obtained product was found to have the following data:
Available iodine content: 0.94 g
Asparagine :1.01 g.

EXAMPLE 5

Preparation of Methionine Iodine

Following a method similar to example 1, 120 ml of ethanol was added, raised the temperature up to 40° C. with stirring, added 2.0 g of acetic acid and 3.5 g of iodine, when dissolved completely, 5.0 g of L-methionine was then introduced gradually, and the mixture was stirred for about 180 minutes, then filtrated, the filtrate is evaporated to remove ethanol and acetic acid, and dried to afford 7.61 g title compound in dark purple.

By analyzing, the obtained product was found to have the following data:
Available iodine content: 3.35 g
Methionine:3.95 g
Gram-molecular ratio of methionine to iodine is 2.01:1.

By structural identification, the obtained product was proved to be a methionine amino-carboxyl complex iodine but not amino complex iodine since it has an infrared absorbed peek at about 1734.6 cm$^{-1}$, which is actually a characteristic of non-ionized carboxyl group, neither L-methionine nor ionic triiodide-complex of L-methionine, however, possess. The following Table 1 showed data of the nuclear magnetic resonance (NMR) spectrum for L-methionine, ionic triiodide-complex of L-methionine and amino-carboxyl complex iodine of L-methionine, which revealed that in the obtained complex product of the present invention, both amino group and carboxyl group take part in the complexing reaction simultaneously. As the result, there forms a non-ionic complex, that is, amino-carboxyl complex iodine of L-methionine.

EXAMPLE 6

Preparation of Tyrosine Iodine

Following a method similar to example 1, 200 ml of water was added, raised the temperature up to 70° C. with stirring, added 0.23 g of tyrosine, and 0.2 g of acetic acid was added under stirring, and 0.5 g of iodine was then introduced gradually, and the mixture was stirred for about 200 minutes, stood for a while, and then filtrated, the filtrate was concentrated and dried to afford 0.33 g title compound.

By analyzing, the obtained product was found to have the following data:
Available iodine content: 0.100 g
Tyrosine : 0.220 g.

EXAMPLE 7

Preparation of Glycine-lysine Iodine

Following a method similar to example 1, 150 ml of water was added, raised the temperature up to 68° C. with stirring, added 3.4 g of glycine and 8.2 g of lysine hydrochloride, when dissolved completely, 2.5 g of hydrochloride acid was added, and 6.2 g of iodine then introduced gradually, and the mixture was stirred for about 128 minutes, then filtrated, the filtrate was concentrated and dried to afford 17.5 g title compound.

By analyzing, the obtained product was found to have the following data:
Available iodine content: 5.5 g
Glycine: 3.3 g
Lysine hydrochloride: 8.0 g.

EXAMPLE 8

Preparation of Multiple Amino-acids Iodine

Multiple amino-acids were obtained at first by hydrolyzing gelatin with hydrochloric acid, with a nitrogen content of 5.87%. Following a method similar to example 1, 85 g of hydrolyzed amino-acids were added, raised the temperature up to 72 ° C. with stirring, 5.5 g of iodine was then added, and the nuxture was stirred for about 192 minutes, then filtrated, the filtrate was concentrated and dried to afford the title compound.

By analyzing, the obtained product was found to have the following data:
Available iodine content: 4.5 g
Nitrogen: 5.7%.

EXAMPLE 9

Preparation of Lysine-glutamate Iodine

Following a method similar to example 1, 110 ml of water was added, raised the temperature up to 65° C. with stirring, added 25 g of lysine-glutamate, when dissolved completely, 3.0 g of fumaric acid was added, and 9.7 g of iodine was then introduced gradually, and the mixture was stirred for about 220 minutes, then filtrated, the filtrate was concentrated and dried to afford 33.4 g title compound.

By analyzing, the obtained product was found to have the following data:
Available iodine content: 8.5 g
Lysine-glutamate : 24.2 g.

An iodine complex with the other simple amino-acids or multiple amino-acids can be prepared by using the similar method as above.

Application Example

According to the present invention, enriched solution of methionine iodine complex was prepared which contains 5% active iodine. 600,000 of *Penaeus vannamei* were raised in a pond with 1.1M depth and 1.6 hectare. Glimmerring was observed at night in the pond, which was proved to be caused by *vibrio splendidus* in water. At the next night, the pond was sterilized using the product prepared according to Example 5 with the content of iodine of 0.01 ppm. The glimmering has disappeared after 40 mins. Methionine iodine complex proved to be very effective in killing *vibrio splendidus*.

According to the present invention, enriched solution of multiplex amino-acid iodine complex was prepared which contains 4% active iodine. 420,000 of *P. momdnon* were raised in a pond with 1.1 hectare. The length of prawns has reached 8.5 cm. Among one hundred prawns, white spot was found on one of them, which was diagnosed to be caused by Baculovirus. White spot disease was controlled after continuously feeding the *P. mondnon* for 4 days with feedstuff which was prepared by mixing 10 g of fish oil and 4 g of multiple amino-acid iodine complex according to Example 8 per kg feedstuff. Thereafter, the *P.mondnon* was fad once a day with said feedstuff. Finally, prawn grown to 12 cm and a good harvest was achieved.

The complex according to the present invention is used widely in the field of aquaculture. Diluted solution of the present invention (0.5% solution) can effectively prevent and treat tomato's epidemic diseases, and can effectively disinfect tableware, medical apparatus and instruments, birds and beasts shed and body skin. It can also be used in the treatment of virus of prawn and fish, hepatitis B virus of human. The present invention has exploited a new approach for the cause of human health.

Although the invention has been illustrated by the preceding embodiments , it is to be understood, however, various modifications and improvements of the invention can be easily made without departing from the principles and spirits of the present invention. Therefore, all of these modifications and improvements should be included in the scope of the appended claims.

TABLE 1

NMR spectrum data of L-methionine and its complex a　　　　b　c　　　d　　　　e
$CH_3-S-CH_2-CH_2-HC-NH_2-COOH$
a　　　　b　c　d

| | a | b | c | d | e |
|---|---|---|---|---|---|
| $^{13}C$ spectrum (ppm) | | | | | |
| L-methionine | 14.419 | 29.339 | 30.181 | 54.407 | 174.440 |
| Ionic triiodide-complex of L-methionine | 15.094 | 30.262 | 30.987 | 54.102 | 173.190 |
| L-methionine iodine | 15.094 | 30.193 | 30.656 | 52.707 | 171.581 |

TABLE 1-continued

NMR spectrum data of L-methionine and its complex

| | a | b | c | d | e | |
|---|---|---|---|---|---|---|
| | CH$_3$—S—CH$_2$—CH$_2$—HC—NH$_2$—COOH | | | | | |
| | a | b | c | d | | |

| | a | b | c | d | e |
|---|---|---|---|---|---|
| complex | | | | | |
| | $^1$H spectrum (ppm) | | | | |
| L-methionine | 2.13 | 2.63 | 2.20 | 3.84 | |
| Ionic triiodide-complex of L-methionine | 2.15 | 2.68 | 2.22 | 4.02 | |
| L-methionine iodine complex | 2.15 | 2.72 | 2.25 | 4.17 | |

What is claimed is:

1. An amino-acid iodine complex comprising an iodine molecule complexed with a plurality of amino acids such that the iodine molecule is at a coordinate center between first and second of said plurality of amino acids with the iodine molecule being complexed to the first and second amino acids at respective amino groups and carboxyl groups of the first and second amino acids, the complex being of general formula (I)

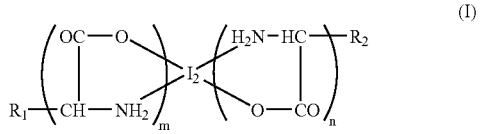

(I)

wherein $R_1$ and $R_2$ may be the same or different and represent side-chain groups of amino-acids, m and n may be the same or different and represent the number of amino-acids in the complex, respectively; and wherein m and n are such that the molecular ratio of amino acid to iodine in the complex is from 2 to 20.

2. The amino-acid iodine complex according to claim 1, wherein the first and second amino acids are simple amino-acids.

3. The amino-acid iodine complex according to claim 2, wherein said simple amino-acids are selected from the group consisting of alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr) and valine (Val).

4. The amino-acid iodine complex according to claim 1, wherein at least said first amino acid is a derivative of a simple amino-acid.

5. The amino-acid iodine complex according to claim 1, wherein at least said first amino acid is formed by simple amino-acids, or multiple amino-acids produced by hydrolyzing animal or plant protein.

6. The amino-acid iodine complex according to claim 1, wherein the iodine molecule at the coordinate center comprises a radioactive isotope.

7. The amino-acid iodine complex according to claim 1, wherein the molecular ratio of amino-acid to iodine is from 2 to 5.

8. The amino-acid iodine complex according to claim 1, wherein the first and second amino acids are methionine, and the molecular ratio of methionine to iodine is 2:1.

9. A method for preparing an amino-acid iodine complex of claim 1, comprising forming an amino-acid amino-carboxyl iodine complex by opening inner-complex ring of amino-acid with an acid catalyst and complexing with the iodine molecule, under suitable conditions of time, medium, temperature and pH value.

10. The method for preparing the amino-acid iodine complex according to claim 9, wherein said acid catalyst is an inorganic acid.

11. The method for preparing the amino-acid iodine complex according to claim 10, wherein said inorganic acid is selected from the group consisting of phosphoric acid, hydrochloric acid and sulfuric acid, said organic acid is selected from citric acid, acetic acid, fumaric acid and lactic acid.

12. The method for preparing the amino-acid iodine complex according to claim 9, wherein the medium comprises water, ethanol, petroleum ether, benzyl alcohol and ethyl acetate.

13. The method for preparing the amino-acid iodine complex according to claim 9, wherein the pH value is from about 1 to 5, the temperature is from about 25 to 85° C., and the time is for a period of from about 30 to 300 mins.

14. The method for preparing the amino-acid iodine complex according to claim 9, wherein said pH value is maintained at a level of from about 2 to 3, said temperature being controlled at from about 40° C. to 50° C., and the time is from about 150 to 200 mins.

15. A composition of disinfectant, comprising the amino-acid iodine complex according to claim 1.

16. A composition of feedstuff, comprising the amino-acid iodine complex according to claim 1.

17. The amino-acid iodine complex according to claim 2, wherein at least said first amino acid is a derivative of a simple amino-acid.

18. The amino-acid iodine complex according to claim 2, wherein at least said first amino acid is formed by simple amino-acids or multiple amino-acids produced by hydrolyzing animal or plant protein.

19. A method for disinfecting an article comprising applying the complex of claim 1 to the article.

* * * * *